United States Patent
Igarashi

(10) Patent No.: US 11,617,524 B2
(45) Date of Patent: Apr. 4, 2023

(54) BLOOD COMPONENT SAMPLING CASSETTE, METHOD FOR MANUFACTURING BLOOD COMPONENT SAMPLING CASSETTE, BLOOD COMPONENT SAMPLING CIRCUIT SET, AND BLOOD COMPONENT SAMPLING SYSTEM

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 660 days.

(21) Appl. No.: 15/999,313

(22) PCT Filed: Feb. 16, 2017

(86) PCT No.: PCT/JP2017/005632
§ 371 (c)(1),
(2) Date: Aug. 16, 2018

(87) PCT Pub. No.: WO2017/142003
PCT Pub. Date: Aug. 24, 2017

(65) Prior Publication Data
US 2019/0038197 A1    Feb. 7, 2019

(30) Foreign Application Priority Data

Feb. 16, 2016 (JP) .............................. JP2016-026994

(51) Int. Cl.
*A61B 5/15* (2006.01)
*A61M 1/36* (2006.01)
*A61M 1/02* (2006.01)

(52) U.S. Cl.
CPC .. *A61B 5/150251* (2013.01); *A61B 5/150267* (2013.01); *A61M 1/0222* (2014.02);
(Continued)

(58) Field of Classification Search
CPC ........ A61B 5/150251; A61B 5/150267; A61M 1/3693; A61M 1/0222; A61M 1/0231;
(Continued)

(56) References Cited

U.S. PATENT DOCUMENTS 5,868,696 A * 2/1999 Giesler ................. A61M 1/303
604/6.12
6,604,908 B1 * 8/2003 Bryant ................. A61M 60/546
417/27
(Continued)

FOREIGN PATENT DOCUMENTS

JP          2013-514863 A    5/2013
WO         02-070035 A2     9/2002
(Continued)

OTHER PUBLICATIONS

International Searching Authority, International Search Report, PCT/JP2017/005632, 3 pages.

*Primary Examiner* — Jessica Arble
(74) *Attorney, Agent, or Firm* — Sheridan Ross P.C.

(57) ABSTRACT

Provided is a blood component sampling cassette which can be efficiently manufactured at low cost compared to a conventional cassette, a method for manufacturing the blood component sampling cassette, a blood sampling circuit set and a blood component sampling system. The blood component sampling cassette includes a cassette main body having a plurality of flow paths including an introduction line, a blood component transfer line and a retransfusion line. The cassette main body includes a first sheet and a second sheet which are formed of a soft material compatible (Continued)

with autoclave sterilization. The first sheet and the second sheet are overlaid in a thickness direction and bonded to each other. A plurality of flow paths is formed between the first sheet and the second sheet.

20 Claims, 10 Drawing Sheets

(52) U.S. Cl.
CPC ........ *A61M 1/0231* (2014.02); *A61M 1/3633* (2013.01); *A61M 1/3693* (2013.01); *A61M 2205/02* (2013.01); *A61M 2205/12* (2013.01); *A61M 2207/00* (2013.01)

(58) Field of Classification Search
CPC ............ A61M 1/3633; A61M 2207/00; A61M 2205/12; A61M 2205/02
See application file for complete search history.

(56) References Cited

U.S. PATENT DOCUMENTS

| | | | |
|---|---|---|---|
| 8,475,138 B2* | 7/2013 | Jones .................... | A61M 60/50 |
| | | | 417/44.2 |
| 2002/0128583 A1* | 9/2002 | Min .................... | A61M 1/3687 |
| | | | 604/6.01 |
| 2005/0049539 A1* | 3/2005 | O'Hara, Jr. ......... | F04B 43/1292 |
| | | | 604/4.01 |
| 2007/0278155 A1* | 12/2007 | Lo .......................... | A61M 1/34 |
| | | | 210/646 |

FOREIGN PATENT DOCUMENTS

| | | |
|---|---|---|
| WO | 2008-033788 A2 | 3/2008 |
| WO | 2009-006471 A2 | 1/2009 |
| WO | 2009-029677 A1 | 3/2009 |
| WO | 2011-084348 A2 | 7/2011 |

\* cited by examiner

BLOOD COMPONENT SAMPLING CASSETTE, METHOD FOR MANUFACTURING BLOOD COMPONENT SAMPLING CASSETTE, BLOOD COMPONENT SAMPLING CIRCUIT SET, AND BLOOD COMPONENT SAMPLING SYSTEM

TECHNICAL FIELD

The present disclosure relates to a blood component sampling cassette which is attached to a blood component separating device, a method for manufacturing the blood component sampling cassette, a blood sampling circuit set and a blood component sampling system.

BACKGROUND ART

Recent blood donation includes whole blood sampling for sampling a whole blood from a blood donor, and component blood sampling (apheresis) which is a light burden for a blood donor. The component blood sampling is a method for using a blood component sampling system (apheresis system), sampling specific blood components from a whole blood and returning the rest of components back to a blood donor body.

Patent Literature 1 discloses a blood component sampling system which centrifuges a whole blood extracted from a blood donor and samples platelets. This blood component sampling system includes a blood sampling circuit set which forms a circuit in which bloods or blood components to be processed flow, and a centrifuge (blood component separating device) to which this blood sampling circuit set is attached. The blood sampling circuit set includes a blood sampling line which includes a blood sampling needle, a belt-shaped channel (separator) in which a whole blood is introduced, a plurality of bags which contains blood components and the like, and a cassette which is connected to the blood sampling line, the channel and the bags with tubes interposed therebetween. In the cassette, a plurality of flow paths including a line which introduces bloods of a blood donor, a line which transfers blood components to the bags, and a retransfusion line which returns the blood components which are not sampled to the blood donor are formed. During use, the cassette is attached to an attachment portion formed in the blood component separating device.

CITATION LIST

Patent Literature

Patent Literature 1: JP 2013-514863 A

SUMMARY OF INVENTION

Technical Problem

A conventional cassette is formed by using a hard resin such as PET which is not resistible against high heat during autoclave sterilization, and therefore is subjected to EOG sterilization as sterilization processing during manufacturing. The EOG sterilization has an issue that a labor and high cost are necessary for sterilization since special process gas is necessary compared to the autoclave sterilization. Further, the conventional cassette has an issue of high cost since the conventional cassette is molded by a large injection molding method.

The present disclosure has been made in light of these issues, and an object of the present disclosure is to provide a blood component sampling cassette which can be efficiently manufactured at low cost compared to a conventional cassette, a method for manufacturing the blood component sampling cassette, a blood sampling circuit set and a blood component sampling system.

Solution to Problem

To achieve the above object, the present disclosure is a blood component sampling cassette which includes a cassette main body having a plurality of flow paths and which is detachably attached to a blood component separating device, and in which the plurality of flow paths includes an introduction line which introduces a blood of a blood donor, a blood component transfer line which transfers to a sampling container a blood component obtained by separating the blood, and a retransfusion line which transfers to the blood donor at least part of the blood component obtained by the separation, the cassette main body includes a first sheet and a second sheet which are formed by using a soft material to which autoclave sterilization is applicable, the first sheet and the second sheet are overlaid in a thickness direction and bonded to each other, and the plurality of flow paths is formed between the first sheet and the second sheet.

The blood component sampling cassette according to the present disclosure employing the above configuration can employ the easy autoclave sterilization as sterilization processing during manufacturing compared to another sterilization processing (e.g. EOG sterilization), and can be efficiently manufactured. Further, by bonding the first sheet and the second sheet made of the soft material by, for example, welding, it is possible to mold the blood component sampling cassette including a plurality of flow paths. Consequently, it is possible to manufacture the blood component sampling cassette at low cost compared to the conventional cassette made of a hard resin manufactured by large injection molding.

In the blood component sampling cassette, the cassette main body may be connected to a plurality of tubes which communicates to the plurality of flow paths respectively, pump function portions on which pump mounted on the blood component separating device work may be located at the tube part which is an inflow side of the plurality of tubes connected to an inflow side of the plurality of flow paths or the area which is an inflow side of the plurality of flow paths of the cassette main body, and a positive pressure may be applied to a side closer to a downstream than the pump function portions are by driving the pumps.

According to the above configuration, the flow paths formed in the cassette main body are not closed during the pump operation, so that no failure occurs during fluid transfer of blood or the like.

In the blood component sampling cassette, the pump function portions may be provided to the tube, and the plurality of flow paths may be configured to be closed when the positive pressure is not applied, and be opened when the positive pressure is applied by bulging flow path formation portions of the first sheet and the second sheet.

According to this configuration, it is not necessary to perform blow molding for forming the flow paths in a manufacturing process, so that it is possible to easily mold the blood component sampling cassette.

In the blood component sampling cassette, at least one of the pump function portions may be provided to the cassette main body and bulge in a normal state.

According to this configuration, the pump function portions are automatically set to the pumps in response to attachment of the blood component sampling cassette to the blood component separating device. Consequently, it is possible to more efficiently attach the blood component sampling cassette to the blood component separating device.

Further, the present disclosure is a blood sampling circuit set which includes: a blood component sampling cassette which is detachably attached to a blood component separating device; a separating processing unit which is connected to the blood component sampling cassette with a tube interposed therebetween, and includes a processing chamber which separates a blood to a plurality of blood components by operating the blood component separating device; and a bag which is connected to the blood component sampling cassette with the tube interposed therebetween, and in which the blood component sampling cassette is one of the above blood component sampling cassettes.

According to this configuration, it is possible to efficiently manufacture the blood sampling circuit set at low cost.

Further, the present disclosure is a blood component sampling system which includes: a blood component separating device; and a blood component sampling cassette which is detachably attached to the blood component separating device, and in which the blood component sampling cassette is the above blood component sampling cassette.

According to this configuration, it is possible to efficiently manufacture the blood component sampling system at low cost.

In the blood component sampling system, the cassette main body may be connected with the plurality of tubes which communicates to the plurality of flow paths respectively, the blood component separating device may include pumps which press the tube part which is an inflow side of the plurality of tubes connected to an inflow side of the plurality of flow paths or the area which is an inflow side of the plurality of flow paths of the cassette main body, and the positive pressure may be applied to a side closer to a downstream than the pump function portions as the pumps press the pump function portions.

In the blood component sampling system, the pumps may be configured and disposed to press the tube part, and the plurality of flow paths may be closed when the positive pressure is not applied, and be opened when the positive pressure is applied by bulging flow path formation portions of the first sheet and the second sheet bulge.

In the blood component sampling system, the pumps may be configured and disposed to press the area of the plurality of flow paths of the cassette main body, and a portion of the cassette main body pressed by the pumps may bulge in a normal state.

Further, the present disclosure is a method for manufacturing a blood component sampling cassette which includes a cassette main body having a plurality of flow paths, and which is detachably attached to a blood component separating device, and includes: overlaying a first sheet and a second sheet formed by using a soft material to which autoclave sterilization is applicable, welding the first sheet and the second sheet to form the plurality of flow paths between the first sheet and the second sheet, and molding the blood component sampling cassette including the cassette main body; and performing autoclave sterilization on the blood component sampling cassette obtained by the molding.

According to this method for manufacturing the blood component sampling cassette, it is possible to manufacture the blood component sampling cassette at low cost compared to the conventional cassette made of the hard resin manufactured by injection molding.

According to the method for manufacturing the blood component sampling cassette, a bag which contains a liquid may be connected to the blood component sampling cassette with a tube interposed therebetween, and the bag may be also subjected to the autoclave sterilization together with the blood component sampling cassette during the sterilization.

Consequently, it is possible to efficiently perform sterilization processing on the blood component sampling cassette and the blood sampling circuit set including the bag.

Advantageous Effects of Invention

According to the present disclosure, it is possible to provide a blood component sampling cassette which can be efficiently manufactured at low cost compared to a conventional cassette, a method for manufacturing the blood component sampling cassette, a blood sampling circuit set and a blood component sampling system.

DESCRIPTION OF EMBODIMENTS

Figure 1:
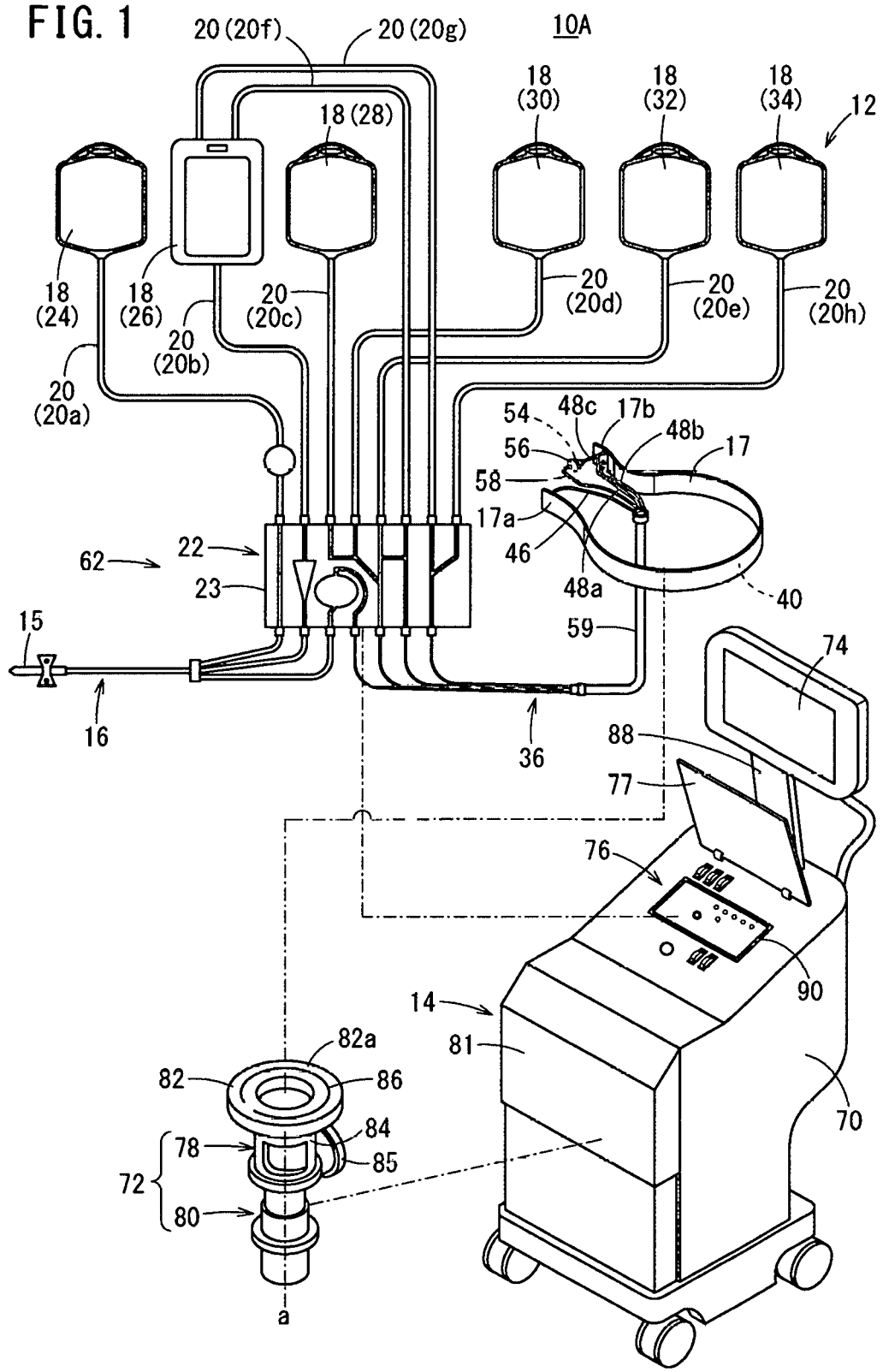
FIG. 1 illustrates a schematic view of a blood component sampling system according to a first embodiment of the present invention.

A blood component sampling cassette, a method for manufacturing the blood component sampling cassette, a blood sampling circuit set and a blood component sampling system according to a plurality of suitable embodiments of the present disclosure will be described with reference to the accompanying drawings. In this regard, the same or similar components in a second embodiment as those in a first embodiment will be assigned the same reference numerals, and will not be described in detail.

First Embodiment

In FIG. 1, a blood component sampling system 10A is configured as a blood apheresis system which continuously extracts bloods (whole blood) from a blood donor, centrifuges the bloods outside a body, samples specific blood components (platelets in the present embodiment) and returns the rest of blood components to the blood donor.

First, the blood component sampling system 10A illustrated in FIG. 1 will be schematically described. This blood component sampling system 10A includes a blood sampling circuit set 12 in which blood components are stored and flow, and a centrifuge 14 (blood component separating device) which applies a centrifugal force to the blood sampling circuit set 12. The blood sampling circuit set 12 includes a channel 17 (blood processing unit) which is a primary separator in which the whole blood extracted from the blood donor is introduced and which centrifuges the whole blood to a plurality of blood components. The centrifuge 14 includes a rotor 78 which applies the centrifugal force to the channel 17. An attachment groove 86 extending in a circumferential direction around a rotation axial center a of the rotor 78 is formed in an upper surface 82a of the rotor 78, and the channel 17 is attachable to the attachment groove 86.

Next, the blood sampling circuit set 12 and the centrifuge 14 will be described in detail.

The blood sampling circuit set 12 is used and discarded every time to prevent contamination and keep sanitation. The blood sampling circuit set 12 includes a blood sampling/retransfusion unit 16 which includes a blood sampling needle 15, the channel 17, a plurality of bags 18, and a blood component sampling cassette 22 (referred to as the "cassette 22" below) connected to these components with a plurality of tubes interposed therebetween. A plurality of bags 18 includes an ACD solution bag 24, a reservoir 26, a platelet preservation solution bag 28, a PPP bag 30, a platelet bag 32 and a red blood cell bag 34.

The blood sampling/retransfusion unit 16 is connected to the ACD solution bag 24 and the reservoir 26 with the cassette 22 interposed therebetween. During use of the blood sampling circuit set 12, an ACD solution which is an anticoagulant agent is supplied from the ACD solution bag 24 to the channel 17 as a default operation, so that the whole blood is prevented from being coagulated.

The channel 17 is connected to the cassette 22 with a channel connection line 36 interposed therebetween. Meanwhile, a plurality of bags 18 is connected to the cassette 22 with a plurality of tubes 20 interposed therebetween.

The channel 17 is formed in a belt-shaped bag, is attached to the attachment groove 86 formed in the rotor 78 of the centrifuge 14, and is configured to allow the blood to be introduced therein, flow and flow out. Further, the channel 17 is a soft bag which includes inside a first chamber 40 (processing chamber) to which the whole blood of the blood donor is supplied, and can be easily bent, folded, rounded. The first chamber 40 extends from one end 17a of the channel 17 to another end 17b.

The one end 17a of the channel 17 is connected with an introduction tube 46 which composes part of the connection line of the channel 17. The introduction tube 46 is connected to the cassette 22. During centrifugation processing, the whole blood introduced in the first chamber 40 is centrifuged by the centrifugal force while the whole blood flows from the one end 17a to the other end 17b.

To sample blood components by using the blood sampling circuit set 12, the whole blood extracted from the blood donor by using the blood sampling needle 15 flows from the one end 17a connected with the introduction tube 46 to the first chamber 40 of the channel 17 attached to the attachment groove 86. The inflow whole blood flows toward the other end 17b along an extension direction of the channel 17. The whole blood receives the centrifugal force in response to rotation of the rotor 78, and is centrifuged while the whole blood flows. In case of the present embodiment, the whole blood is centrifuged to plasma (platelet poor plasma: PPP) which is light specific gravity components (supernatant components), red blood cells (concentrated red cells) which are heavy specific gravity components (sedimentation components), and buffy coat (BC) which is intermediate specific gravity components.

The other end 17b of the channel 17 is connected with first to third lead tubes 48a to 48c. The first lead tube 48a and the second lead tube 48b are connected to the cassette 22. The red blood cells centrifuged in the first chamber 40 are introduced in the cassette 22 via the first lead tube 48a. Further, the plasma generated in the first chamber 40 is introduced in the cassette 22 via the second lead tube 40b.

The third lead tube 48c is connected to a concentrator 56 which is a secondary separator including a second chamber 54. The buffy coat generated in the first chamber 40 by centrifuging the whole blood is introduced in the concentrator 56 via the third lead tube 48c. The buffy boat includes white blood cell components and platelet rich plasma (platelet containing components).

The concentrator 56 introduces the buffy coat in the second chamber 54 from the channel 17, and further centrifuges the buffy coat by the centrifugal force caused by the rotation of the rotor 78. This concentrator 56 is formed in a conical shape with a plurality of steps, and, in a state where the concentrator 56 is attached to the rotor 78, a top side of the conical shape is disposed at a far side from a centrifugal center and a bottom side of the conical shape is disposed at a near side to the centrifugal center.

The concentrator 56 centrifuges the buffy coat to the white blood cells which are the heavy specific gravity components, and platelets which are light specific gravity components (more specifically, the platelet containing components including plasma and platelets). The white blood cells are captured by a plurality of steps formed in the concentrator 56. The platelets flow out to a relay tube 58 connected to an outlet (bottom side) of the concentrator 56, and is introduced in the cassette 22.

In this regard, the introduction tube 46, the first lead tube 48a, the second lead tube 48b and the relay tube 58 are bundled by a bundling sheath 59. In the present embodiment, a channel connection line 36 is composed of the introduction tube 46, the first to third lead tubes 48a to 48c, the concentrator 56 and the relay tube 58.

The ACD solution bag 24 is a bag which contains the ACD solution which is an anticoagulant agent, and is connected to the cassette 22 with a tube 20a interposed therebetween. The reservoir 26 is a container in which the blood components to be returned to the blood donor are temporarily stored, and is connected to the cassette 22 with a tube 20b interposed therebetween. During centrifugation processing, the red blood cells and the plasma are introduced and temporarily stored in the reservoir 26 via tubes 20f and 20g. The red blood cells and the plasma are returned to the blood donor from the reservoir 26 via the cassette 22 after the centrifugation processing. In this regard, the reservoir 26 is not limited to a form of a bag (soft container) and may be configured as a form of a hard container such as a tank.

The platelet preservation solution bag 28 is a bag which contains a platelet preservation solution (PAS solution), and is connected to the cassette 22 with a tube 20c interposed therebetween. The PPP bag 30 is a bag which contains plasma obtained by the centrifugation, and is connected to the cassette 22 with a tube 20*d* interposed therebetween.

The platelet bag 32 is a bag which contains the platelets obtained by the centrifugation, and is connected to the cassette 22 with a tube 20*e* interposed therebetween. The red blood cell bag 34 is a bag which contains the red blood cells obtained by the centrifugation, and is connected to the cassette 22 with a tube 20*h* interposed therebetween.

Figure 3:
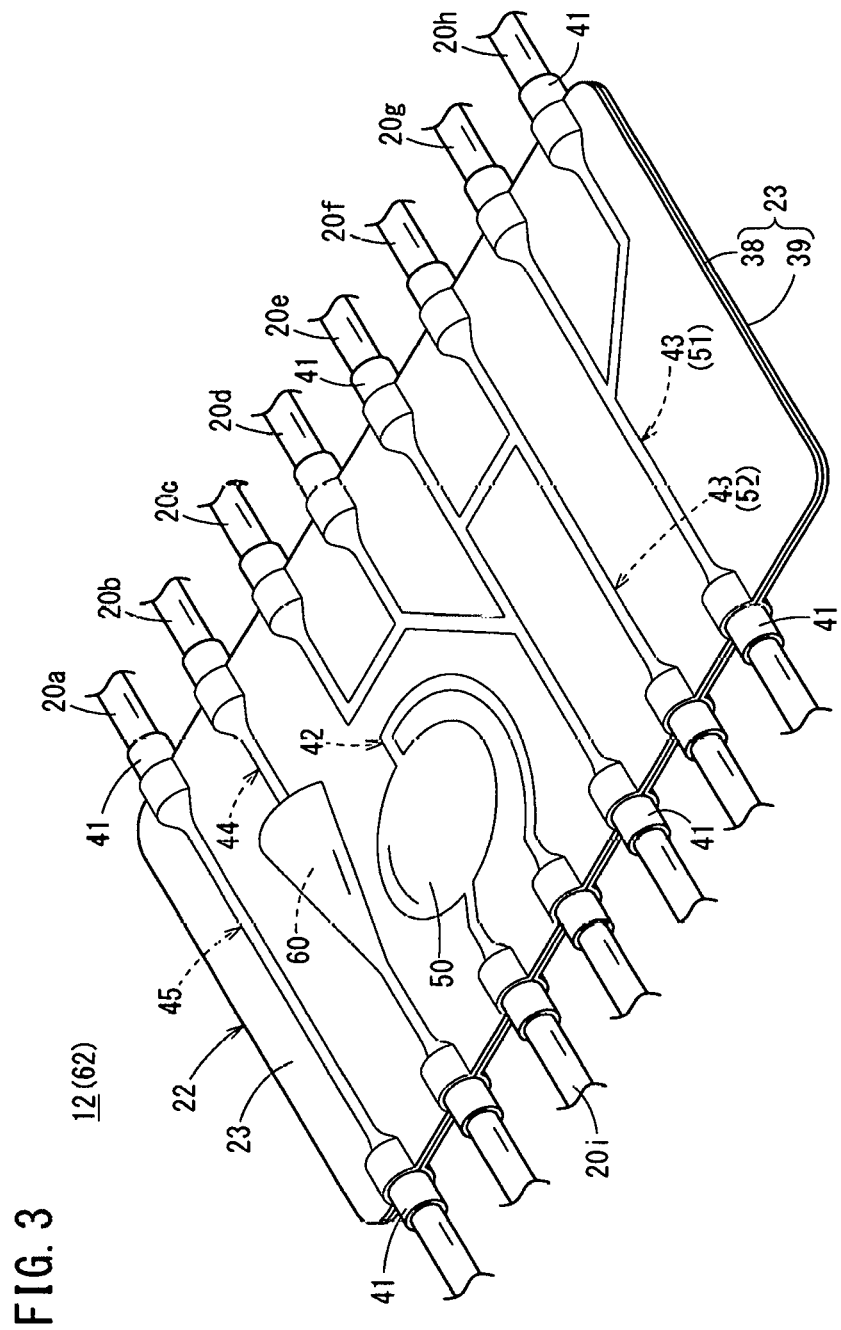
FIG. 3 illustrates a perspective view of a blood component sampling cassette according to the first embodiment of the present disclosure.

In FIG. 3, the cassette 22 includes a cassette main body 23 having a plurality of flow paths. The cassette main body 23 includes a first sheet 38 and a second sheet 39 which are formed by using a soft material to which autoclave sterilization is applicable. The first sheet 38 and the second sheet 39 are overlaid in a thickness direction and bonded to each other.

That autoclave sterilization is applicable to the soft material which composes the first sheet 38 and the second sheet 39 means that the soft material has heat resistance against heat of the autoclave sterilization (e.g. 121° C.) for a predetermined time or more, and a water vapor permeability which allows water vapor which is process gas to be introduced in flow paths in the cassette 22. Such a soft material includes, for example, vinyl chloride and polyolefin.

A plurality of flow paths is formed between the first sheet 38 and the second sheet 39. Means for bonding the first sheet 38 and the second sheet 39 includes, for example, welding (high frequency welding, ultrasonic welding, thermal welding or the like) and adhesion. Further, the cassette 22 includes a plurality of port members 41 disposed at a periphery of the cassette main body 23, and tubes (tube 20 or the like) are connected to these port members 41, respectively.

Figure 2:
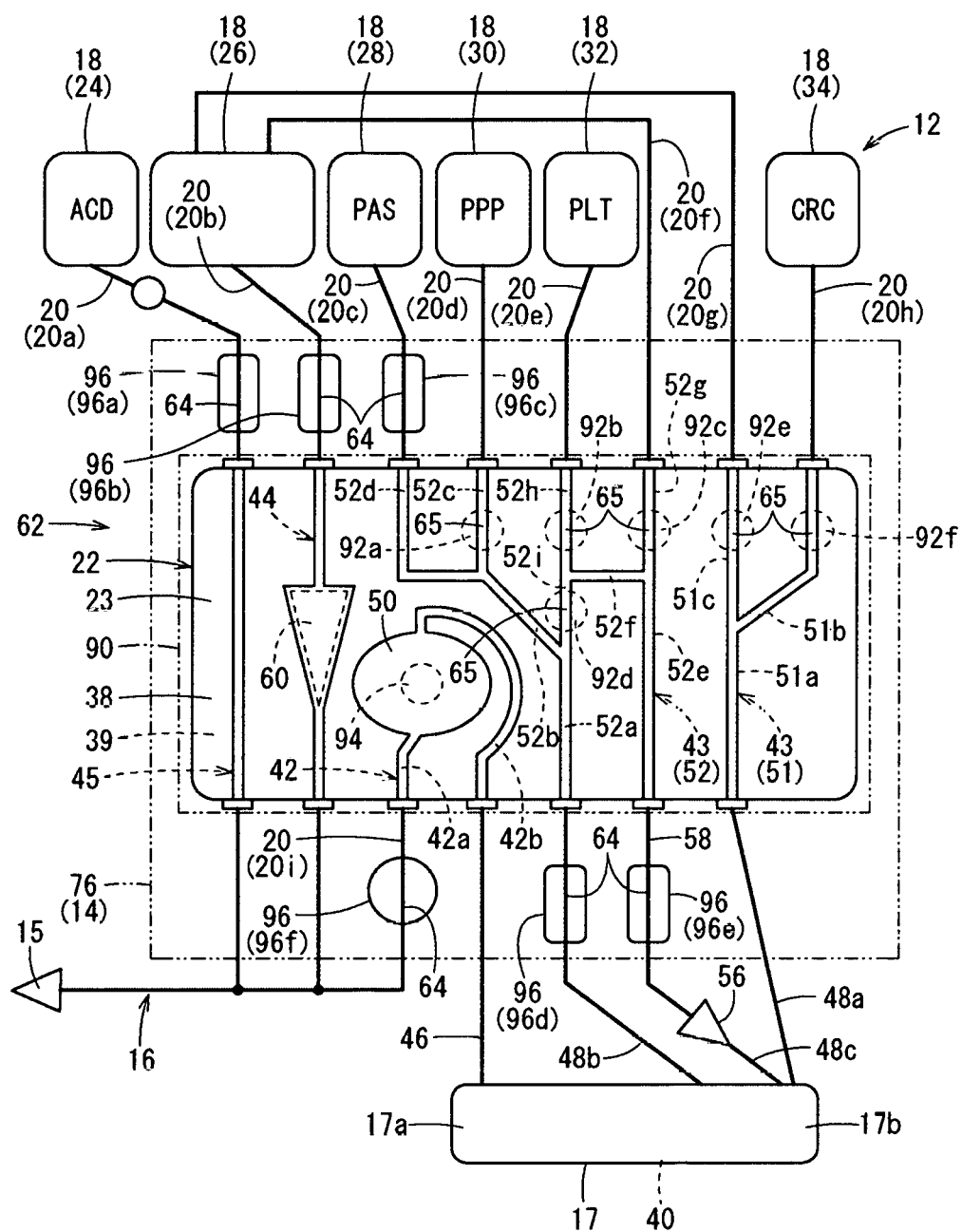
FIG. 2 illustrates a circuit configuration diagram of the blood component sampling system illustrated in FIG. 1.

As illustrated in FIG. 2, a plurality of flow paths formed in the cassette main body 23 includes at least an introduction line 42 which introduces the blood sampled from the blood donor, a blood component transfer line 43 which transfers the blood components obtained by separating the blood to sampling containers (the PPP bag 30, the platelet bag 32 and the red blood cell bag 34), and a retransfusion line 44 which transfers the blood components which are not sampled, to the blood donor. In the present embodiment, a plurality of flow paths includes an ACD solution line 45 which transfers the ACD solution to the blood sampling/retransfusion unit 16.

An inflow side (flow path element 42*a*) of the introduction line 42 is connected with a tube of the blood sampling/retransfusion unit 16. An outflow side (flow path element 42*b*) of the introduction line 42 is connected with the introduction tube 46 connected to the channel 17. Hence, the blood sampling/retransfusion unit 16 and the channel 17 are connected with the introduction line 42 interposed therebetween. Further, a balloon unit 50 which can expand and contract is provided on the introduction line 42. The balloon unit 50 is a portion pressed by a centrifugal pressure sensor 94 (see FIG. 6) described below and provided to the centrifuge 14. Parts of the first sheet 38 and the second sheet 39 compose a wall of the balloon unit 50. A lumen of the balloon unit 50 communicates to the flow path element 42*a* and the flow path element 42*b*

The blood component transfer line 43 includes a first line 51 and a second line 52 which are independent from each other. A flow path element 51*a* which composes an inflow side of the first line 51 is connected to the first lead tube 48*a* connected to the channel 17. An outflow side of the first line 51 is composed of flow path elements 51*b* and 51*c* branched from the flow path element 51*a*. The flow path element 51*b* is connected to the tube 20*h* connected to the red blood cell bag 34. The flow path element 51*c* is connected to the tube 20*g* connected to the reservoir 26. Hence, the red blood cells separated in the channel 17 can be transferred to the red blood cell bag 34 via the flow path elements 51*a* and 51*b*, and can be transferred to the reservoir 26 via the flow path elements 51*a* and 51*c*.

The second line 52 is connected to the second lead tube 48*b*, the relay tube 58 and the tubes 20*c* to 20*f*. More specifically, the second line 52 includes a flow path element 52*a* which is connected to the second lead tube 48*b*, a flow path element 52*b* which is branched from the flow path element 52*a*, a flow path element 52*c* which is connected with the tube 20*d* connected to the PPP bag 30 and continues to the flow path element 52*b*, and a flow path element 52*d* which is connected with the tube 20*e* connected to the platelet preservation solution bag 28 and continues to the flow path element 52*b*. The second lead tube 48*b* is connected to the inflow side of the flow path element 52*a*. The tube 20*c* is connected to the inflow side of the flow path element 52*d*.

The second line 52 further includes a flow path element 52*e* which is connected with the relay tube 58, a flow path element 52*f* and a flow path element 52*g* which are branched from the flow path element 52*e*, a flow path element 52*h* which continues to the flow path element 52*f*, and is connected with the tube 20*e* connected to the platelet bag 32, and a flow path element 52*i* which is branched from the flow path element 52*a* and continues to the flow path element 52*f* and the flow path element 52*h*. The flow path element 52*g* is connected with the tube 20*g* connected to the reservoir 26. The relay tube 58 is connected to the inflow side of the flow path element 52*e*.

The plasma separated in the channel 17 can be transferred to the PPP bag 30 via the flow path elements 52*a* to 52*c* in the cassette 22. Further, the plasma separated in the channel 17 can be transferred to the reservoir 26 via the flow path elements 52*a*, 52*i*, 52*f* and 52*g* in the cassette 22. The platelets separated in the channel 17 can be transferred to the platelet bag 32 via the flow path elements 52*e*, 52*f* and 52*h* in the cassette 22. A platelet preservation solution can be transferred to the platelet bag 32 via the flow path elements 52*d*, 52*b*, 52*i* and 52*h* in the cassette 22.

An inflow side of the retransfusion line 44 is connected with the tube 20*b* connected to the reservoir 26. An outflow side of the retransfusion line 44 is connected with the blood sampling/retransfusion unit 16. Hence, the blood sampling/retransfusion unit 16 and the reservoir 26 are connected via the retransfusion line 44. A filter member 60 which removes foreign materials such as coagulated blood clots included in the blood components passing through the reservoir 26 is disposed on a flow path of the retransfusion line 44 in the cassette main body 23.

In the present embodiment, the flow paths provided in the cassette 22 may be flow paths which are open in a normal state or may be flow paths which are closed when a positive pressure is not applied and are opened when the positive pressure is applied. In case of the former flow paths, even when the positive pressure is not applied, flow path formation portions of the first sheet 38 and the second sheet 39 bulge in protrusion shapes in a thickness direction of the cassette 22. In case of the latter flow paths, when the positive pressure is not applied, the flow path formation portions of the first sheet 38 and the second sheet 39 are nearly flat, and, when the positive pressure is applied, the flow path formation portions of the first sheet 38 and the second sheet 39 bulge in protrusion shapes.

An assembly composed of the cassette 22 and tubes (tube 20 or the like) connected to the cassette 22 in the blood sampling circuit set 12 will be referred to as a "cassette/tube assembly 62".

In FIG. 2, tubes (tube part which is an inflow side) connected to the inflow sides of a plurality of flow paths of the tubes connected to the cassette main body 23 are provided with pump function portions 64 on which pumps 96 provided to the centrifuge 14 work. Each pump function portion 64 is disposed at the inflow side of the flow path formed in the cassette 22. By driving each pump 96, the positive pressure is applied to a side closer to a downstream than each pump function portion 64 of the flow path formed in the cassette main body 23 is.

In the present embodiment, the tubes 20a to 20c and 20i connected to the inflow sides of the ACD solution line 45, the retransfusion line 44 and the introduction line 42, and the tubes (the second lead tube 48b and the relay tube 58) connected to the inflow sides of the second line 52 are provided with the pump function portions 64. The pump function portions 64 are portions of the tubes 20a to 20c, 20i, the second lead tube 48b and the relay tube 58 which the pumps 96 are attached to (contact), need to have forms of normal tubes and do not need to employ a special configuration.

The cassette 22 is provided with a plurality of clamp function portions 65 on which a plurality of clamps 92 provided to the centrifuge 14 works. When the cassette 22 is attached to the centrifuge 14, each clamp function portion 65 contacts or faces each corresponding clamp 92. More specifically, the clamp function portions 65 are provided at portions of the cassette 22 at which the flow path elements 51b and 51c of the first line 51 are formed, and are provided at portions of the cassette 22 at which the flow path elements 51c, 51g, 51h and 51i of the second line 52 are formed.

In this regard, a configuration of the flow paths formed in the cassette 22, and the number and an arrangement of the bags to be provided are not limited to the above and illustrated configuration, and may be modified according to types of blood components to be sampled and a use method. When, for example, the red blood cells are not sampled, the red blood cell bag 34 may be removed. Further, the ACD solution bag 24 may be detached from the cassette 22 in a default state and may be connected to the cassette 22 when a user connects the tube 20a with a connection needle to the ACD solution bag 24 to use.

In FIG. 1, the centrifuge 14 is a device which is repeatedly used to sample blood components, and is equipped at medical facilities, blood sampling vehicles and the like. The centrifuge 14 includes a box-shaped device main body 70 which is formed relatively long in a height direction, a monitor 74 which is supported by a support column 88 protruding upward from an upper rear side of the device main body 70, an attachment portion 76 which is configured to allow the cassette/tube assembly 62 of the blood sampling circuit set 12 to be attached thereto, a cover body 77 which is openable, and is configured to cover the attachment portion 76 when closed, a centrifugal unit 72 which is housed in the device main body 70, and a door 81 which can open and close a front surface side of the device main body 70.

The device main body 70 allows a plurality of bags 18 of the blood sampling circuit set 12 to be hanged and held thereto, and has a function of controlling centrifugation of bloods extracted in the blood sampling circuit set 12.

The monitor 74 is, for example, a touch panel type, and functions not only as display means which displays an operation state and the like of the device main body 70 for centrifuging the bloods, and input means which receives an input of an instruction for operating the device main body 70.

Figure 4:
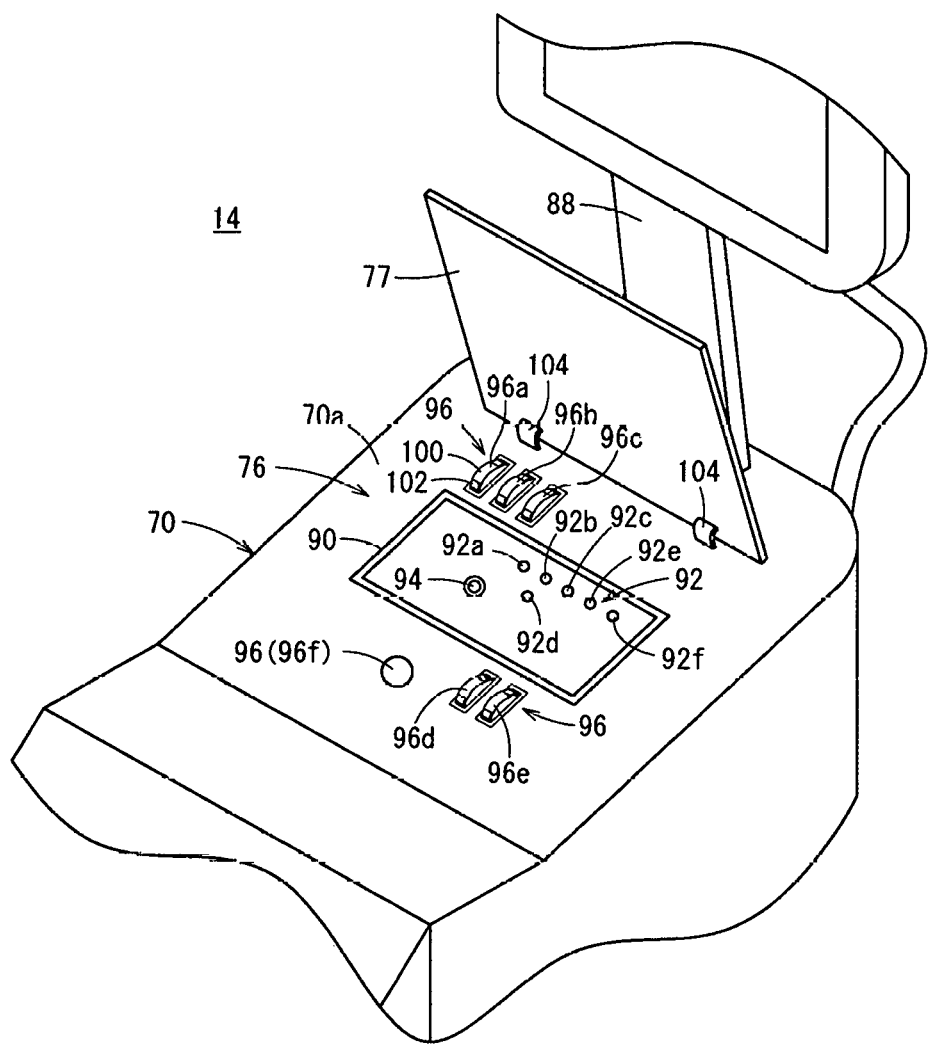
FIG. 4 illustrates a perspective view that illustrates a configuration of an attachment portion of a centrifuge in the blood component sampling system illustrated in FIG. 1.

In FIG. 4, the attachment portion 76 is disposed at a side of an upper portion of the device main body 70. In the present embodiment, the attachment portion 76 includes a cassette holding portion 90 which is configured to hold the cassette 22, a plurality of clamps 92 (92a to 92f) which is configured to press the clamp function portions 65 provided to the cassette 22, the centrifugal pressure sensor 94 which detects a centrifugal pressure, and pumps 96 which work on the tubes connected to the inflow side of a plurality of flow paths provided to the cassette 22.

For example, the cassette holding portion 90 may include a plurality of pins and be configured to hold the cassette 22 when a plurality of pins is inserted in holes provided at the periphery of the cassette 22, or may be configured to hold the cassette 22 by sandwiching the periphery of the cassette 22. When the cover body 77 is closed in a state where the cassette 22 is held by the cassette holding portion 90, the cassette 22 is sandwiched between a housing of the device main body 70 and the cover body 77.

A plurality of clamps 92 (92a to 92f) is provided to the cassette holding portion 90. Each clamp 92 can move back and forth in the thickness (an arrow A direction in FIG. 5A) of the cassette 22 in a state where each clamp 92 is held by the cassette holding portion 90, and is disposed to meet each of a plurality of clamp function portions 65 provided to the cassette 22.

Figure 5A:
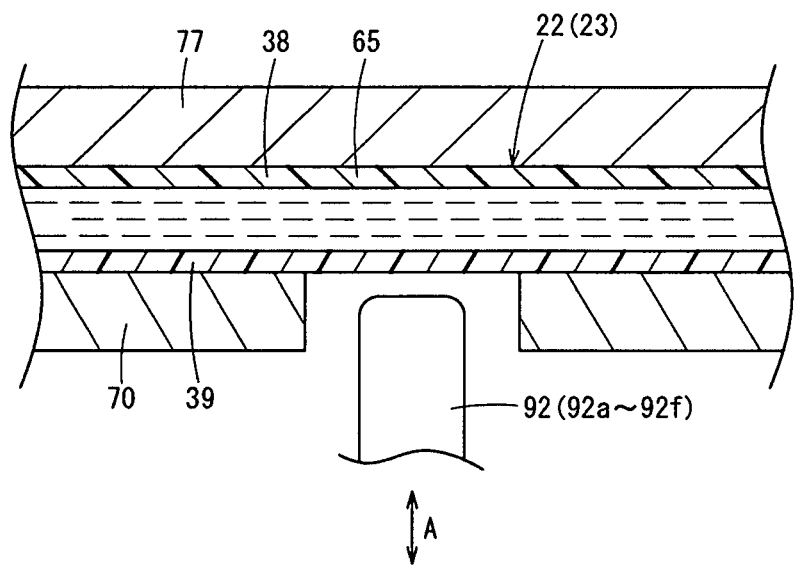
FIG. 5A illustrates a first view for explaining a clamp function provided to the centrifuge.
Figure 5B:
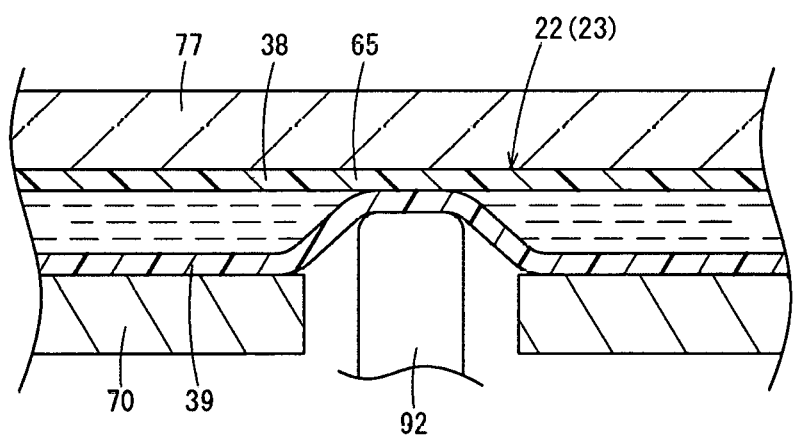
FIG. 5B illustrates a second view for explaining clamp function provided to the centrifuge.

When each clamp 92 moves back as in FIG. 5A, each clamp function portion 65 is not pressed, and the flow path at the portion at which each clamp function portion 65 is provided is opened. When each clamp 92 protrudes and presses the clamp function portion 65 as in FIG. 5B, the cover body 77 and the clamp 92 sandwich and press each clamp function portion 65, so that the flow path at the portion at which the clamp function portion 65 is provided is closed. When each clamp 92 moves back from the state in FIG. 5B, an elastic restoration force of the cassette main body 23 (clamp function portion 65) restores each clamp function portion 65 to the original shape, and the flow path is opened.

Figure 6:
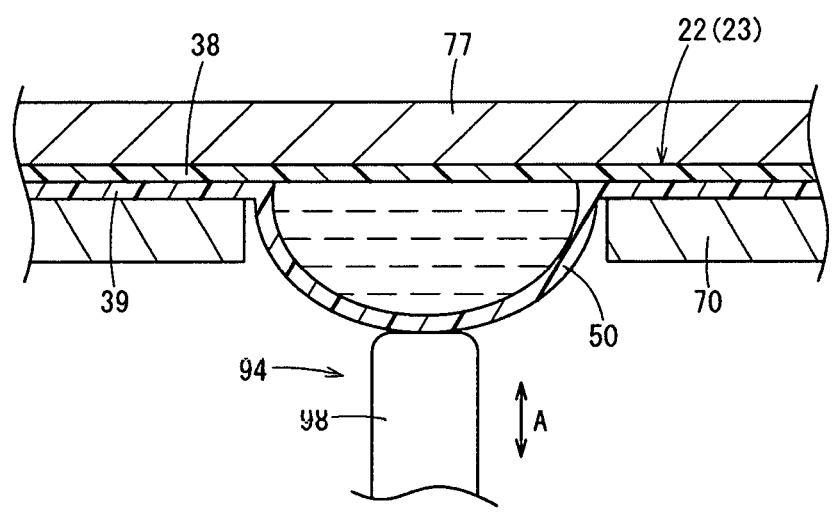
FIG. 6 is a functional explanatory view of a separating pressure sensor provided to the centrifuge.

In FIG. 4, the centrifugal pressure sensor 94 is provided to the cassette holding portion 90. As illustrated in FIG. 6, the centrifugal pressure sensor 94 includes a detection bar 98 which comes into contact with the balloon unit 50 of the cassette 22 in a state where the centrifugal pressure sensor 94 is held by the cassette holding portion 90. The detection bar 98 is movable in the thickness direction (A direction) of the cassette 22, and is pressed by the balloon unit 50. Consequently, it is possible to detect a centrifugal pressure (a pressure in the processing chamber 40) based on the position of the detection bar 98.

In FIG. 2, a plurality of pumps 96 is disposed near the cassette holding portion 90 such that a plurality of pumps 96 is attached to the tubes 20a to 20c, 20i, the introduction tube 46 and the relay tube 58 connected to the inflow sides of the ACD solution line 45, the retransfusion line 44, the introduction line 42, and the blood component transfer line 43 of the second line 52 (also see FIG. 4). In the present embodiment, the pumps 96a to 96e which work on the tubes 20a to 20c, the introduction tube 46 and the relay tube 58 adopt a roller pump mode which causes a liquid (blood components or the like) in the tubes to flow by repeatedly pressing the tubes.

In FIG. 4, the pumps 96a to 96e adopting the roller pump mode include wheels 100 which are driven to rotate, and rollers 102 which are rotatably provided at intervals in the circumferential direction at the outer circumferences of the wheels 100. Each roller 102 moves in the circumferential direction crushing the tube as each wheel 100 rotates, so that a liquid flows in the tube.

In the present embodiment, the pumps 96a to 96e adopting the roller pump mode are disposed such that rotary axis lines of the wheels 100 are parallel to a housing outer surface 70a composing the attachment portion 76, and the outer circumferences of the wheel 100 are partially exposed from the housing outer surface 70a. When the cassette 22 is held by the cassette holding portion 90, the tubes (the tube 20 or the like) provided with the pump function portions 64 are placed on the roller pumps (wheels 100) and the cover body 77 is closed, the tubes (the tube 20 or the like) are sandwiched between the cover body 77 and the roller pumps.

In this regard, in a modified example, the roller pumps (pumps 96a to 96e) may be installed such that the rotary axis lines of the wheels 100 are vertical with respect to the housing outer surface 70a composing the attachment portion 76.

The pump 96f which works on the tube 20i connected to the inflow side of the introduction line 42 is a pump (referred to as a "blood sampling pump 96f") which extracts the bloods from the blood donor and transfers the bloods to the channel 17 via the introduction line 42. The blood sampling pump 96f may be a roller pump similar to the other pumps 96a to 96e or may be pumps (diaphragm pumps or the like) of other modes.

In this regard, when the diaphragm pump is adopted as the blood sampling pump 96f, two check valves are provided to the tubes 20i at an interval, and a diaphragm portion of the diaphragm pump is connected to the tube 20i between the two check valves. Further, the diaphragm pump can function as a donor pressure sensor, too, which detects a blood pressure (donor pressure) of the blood donor based on a fluctuation amount of the diaphragm portion.

One end of the cover body 77 is rotatably jointed to the device main body 70 with hinge portions 104 interposed therebetween. The cover body 77 is configured to lock the closed state. The cover body 77 is preferably composed of a hard material. Further, when the cover body 77 is composed of a transparent material, it is possible to visually check the cassette/tube assembly 62 attached to the attachment portion 76 even in the closed state of the cover body 77, and visually check the state of the cassette/tube assembly 62.

In addition, the cover body 77 illustrated in FIG. 4 has one flat shape body and is configured to cover a target range. However, according to a modified example of the cover body 77, the cover body 77 may have a plurality of (e.g. two) flat shape bodies which is individually openable, and is configured to cover a target range by a plurality of flat shape bodies.

In FIG. 1, the centrifugal unit 72 includes the rotor 78 which is rotatable about a vertical axial center, and a driving unit 80 (motor) which drives and rotates this rotor 78. The rotor 78 includes an upper rotor 82 to which the channel 17 is attached, and a lower rotor 84 which is coaxially rotatable with the upper rotor 82. The upper rotor 82 is relatively rotatable with respect to the lower rotor 84, and an attachment groove 86 to which the channel 17 is attached is formed in an upper surface 82a of the upper rotor 82.

The lower rotor 84 is coupled to an output axis of the driving unit 80. The upper rotor 82 and the lower rotor 84 are coupled by a pinion assembly 85 to rotate the upper rotor 82 at a double speed compared to the lower rotor 84. The pinion assembly 85 includes, for example, an intermediate gear which is supported by the lower rotor 84 rotatably about the axial center vertical to the rotation axial center a of the rotor 78, a lower gear which is provided to a non-rotation portion and enmeshes with a lower portion of the intermediate gear, and an upper gear which is provided to the upper rotor 82 about the rotation axial center a.

This pinion assembly 85 rotates the upper rotor 82 two times every time the lower rotor 84 rotates once. Consequently, even when the channel 17 is continuously rotated by the rotor 78 due to centrifugation, a twist between the channel 17 and a plurality of tubes such as the introduction tube 46 connected to this channel 17 settles in a predetermined range. Hence, a rotary seal between the channel 17 and a plurality of tubes such as the introduction tube 46 is not necessary.

The cassette 22 employing the above configuration can be manufactured by, for example, the following manufacturing method. The method for manufacturing the cassette 22 according to the present embodiment includes a molding process of overlaying the first sheet 38 and the second sheet 39, welding the first sheet 38 and the second sheet 39 to form a plurality of flow paths between the first sheet 38 and the second sheet 39, and molding the cassette 22 including the cassette main body 23, and a sterilizing process of sterilizing the cassette 22 obtained by the molding process.

Figure 7:
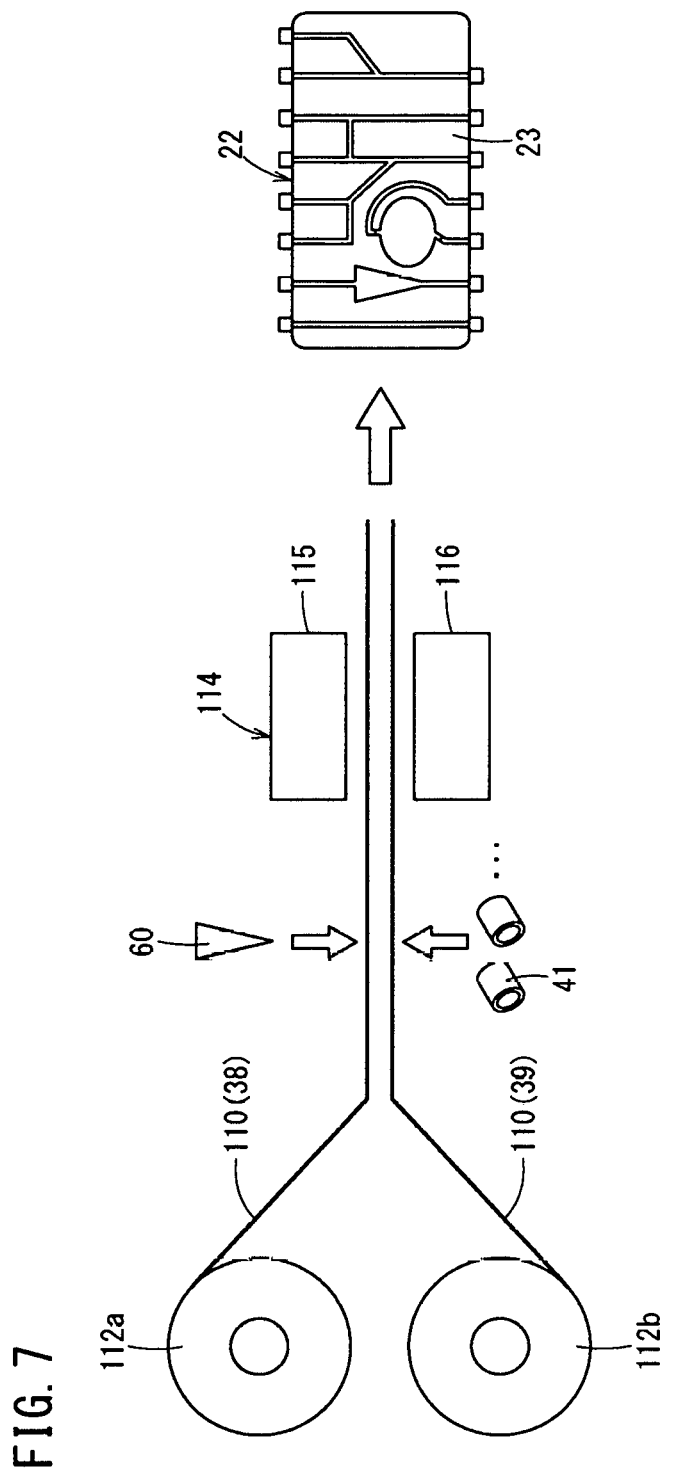
FIG. 7 illustrates a view for explaining a molding process of a method for manufacturing the blood component sampling cassette.

As illustrated in FIG. 7, in the molding process, sheet materials 110 are fed from two material rolls 112a and 112b formed by winding the sheet materials 110 which are materials of the first sheet 38 and the second sheet 39, and are supplied together with assembling parts (the filter member 60 and the port members 41) to a bonding device 114 such as a high frequency welding device. The bonding device 114 includes upper and lower molds 115 and 116, and molds the cassette 22 having a plurality of flow paths by bonding the two overlaid sheet materials 110 together with the assembling parts. In this case, when the bonding device 114 molds the cassette 22, the tubes (the tube 20 or the like) may be connected.

In the sterilizing process, the cassette 22 obtained by the molding process is subjected to autoclave sterilization. The cassette 22 is made of a material which is resistible against heat of the autoclave sterilization, and therefore does not melt due to heat during sterilization. Further, the cassette 22 is composed of a material having water vapor permeability, and therefore allows the water moisture which is process gas of the autoclave sterilization to be introduced in the flow paths of the cassette 22. Consequently, it is possible to suitably sterilize the cassette 22.

In the sterilizing process, the entire blood sampling circuit set 12 including a plurality of bags 18 (the ACD solution bag 24 and the like) may be subjected to the autoclave sterilization. Consequently, it is possible to efficiently sterilize the blood sampling circuit set 12.

Next, a function and an effect of the blood component sampling system 10A according to the present embodiment employing the above configuration will be described.

The blood sampling circuit set 12 is attached to the centrifuge 14 to prepare for (set up) sampling of blood components from the blood donor by using the blood component sampling system 10A illustrated in FIG. 1. More specifically, the blood sampling circuit set 12 is attached to the centrifuge 14 by attaching the cassette/tube assembly 62 to the attachment portion 76, hanging a plurality of bags 18 on the centrifuge 14 and attaching the channel 17 to the rotor 78. Meanwhile, the blood sampling needle 15 punctures the blood donor.

In this regard, after the cassette/tube assembly 62 is attached to the attachment portion 76, the cover body 77 is closed. Thus, the cassette/tube assembly 62 is sandwiched between the cover body 77 and the attachment portion 76, the pump function portions 64 are set to the pumps 96, and the clamp function portions 65 are disposed facing the clamps 92.

In FIG. 2, when the user operates and instructs the centrifuge 14 to start operating, the centrifuge 14 transfers the ACD solution in the ACD solution bag 24 to the ACD solution line 45 in the cassette 22 via the tube 20*a* under an action of the pump 96*a*, and supplies the ACD solution to the blood sampling/retransfusion unit 16, the introduction line 42 and the channel 17. Thus, it is possible to prevent the bloods from coagulating in the circuit.

Next, the centrifuge 14 applies the centrifugal force to the channel 17 attached to the rotor 78 by rotating the rotor 78, operating the blood sampling pump 96*f*, thereby extracting the bloods (whole blood) from the blood donor and introducing the bloods in the channel 17 in the introduction line 42 and the introduction tube 46. The bloods introduced in the channel 17 are separated to red blood cells, buffy coat and plasma by the centrifugal force while the bloods flow from the one end 17*a* to the other end 17*b*.

The red blood cells separated in the channel 17 are introduced in the first line 51 of the cassette 22 via the first lead tube 48*a*, part of the red blood cells are introduced in the red blood cell bag 34 via the tube 20*h* and the rest of red blood cells are introduced in the reservoir 26 via the tube 20*g*. In this case, the centrifuge 14 introduces the red blood cells in the red blood cell bag 34 via the flow path elements 51*a* and 51*b* by opening the clamp 92*f* and closing the clamp 92*e*. Further, the centrifuge 14 introduces the red blood cells in the reservoir 26 via the flow path elements 51*a* and 51*c* by opening the clamp 92*e* and closing the clamp 92*f*.

The plasma separated in the channel 17 is introduced in the second line 52 of the cassette 22 via the second lead tube 48*b* under an action of the pump 96*d*, part of the plasma is introduced in the PPP bag 30 via the tube 20*d* and the rest of the plasma is introduced in the reservoir 26 via the tube 20*f*. In this case, the centrifuge 14 introduces the plasma in the PPP bag 30 via the flow path elements 52*a* to 52*c* by opening the clamp 92*a* and closing the clamp 92*d* among the clamps 92 provided to the second line 52. Further, the centrifuge 14 introduces the plasma in the reservoir 26 via the flow path elements 52*a*, 52*i*, 52*f* and 52*g* by opening the clamps 92*c* and 92*d* and closing the clamps 92*a* and 92*b*.

The buffy coat separated in the channel 17 is introduced in the concentrator 56 via the third lead tube 48*c* under an action of the pump 96*e*, and is separated to white blood cells and platelets by the concentrator 56. Further, the separated platelets are introduced in the second line 52 of the cassette 22 via the relay tube 58 under the action of the pump 96*e*, and are introduced in the platelet bag 32 via the tube 20*e*. In this case, the centrifuge 14 introduces the platelets in the platelet bag 32 via the flow path elements 52*c*, 52*f* and 52*h* by opening the clamp 92*b* and closing the clamps 92*c* and 92*d* among the clamps 92 provided to the second line 52.

Further, before or after the platelets are introduced in the platelet bag 32, the platelet preservation solution (PAS solution) in the platelet preservation solution bag 28 is introduced in the second line 52 of the cassette 22 via the tube 20*c* under an action of the pump 96*c*, and is supplied to the platelet bag 32 via the tube 20*e*. In this case, the centrifuge 14 introduces the platelet preservation solution in the platelet bag 32 via the flow path elements 52*d*, 52*b*, 52*i* and 52*h* by opening the clamps 92*b* and 92*d* and closing the clamps 92*a* and 92*c* among the clamps 92 provided to the second line 52.

The blood components (the red blood cells and the plasma) stored in the reservoir 26 are introduced in the retransfusion line 44 in the cassette 22 via the tube 20*b* under an action of the pump 96*b*, and is returned to the blood donor via the blood sampling/retransfusion unit 16. In this case, foreign materials such as coagulated blood clots included in the blood components passing through the reservoir 26 are trapped by the filter member 60 provided to the retransfusion line 44, so that it is possible to reduce a risk caused when the foreign materials return to the blood donor.

As described above, the cassette 22 according to the present embodiment can employ the easy autoclave sterilization as sterilization processing during manufacturing compared to another sterilization processing (e.g. EOG sterilization), and can be efficiently manufactured. Further, by, for example, welding the first sheet 38 and the second sheet 39 made of the soft material, it is possible to manufacture the cassette 22. Consequently, it is possible to manufacture the cassette at low cost compared to the conventional cassette made of a hard resin manufactured by injection molding.

Further, in the present embodiment, the tubes connected to the inflow sides of a plurality of flow paths formed in the cassette main body 23 are provided with the pump function portions 64 on which the pumps 96 (96*a* to 96*f*) of the centrifuge 14 work, so that a positive pressure is applied to the side closer to the downstream than the pump function portions 64 are by driving the pumps 96. According to the above configuration, the flow paths formed in the cassette main body 23 are not closed during the pump operation, so that no failure occurs during fluid transportation of blood.

Further, in the present embodiment, a plurality of flow paths formed in the cassette main body 23 is configured to be closed when the positive pressure is not applied, and be opened when the positive pressure is applied by bulging the flow path formation portions of the first sheet 38 and the second sheet 39. According to this configuration, it is not necessary to perform blow molding for forming the flow paths in the manufacturing process, so that it is possible to easily mold the cassette 22.

In the present embodiment, a plurality of roller pumps (pumps 96*a* to 96*e*) is disposed vertically at the attachment portion 76 of the centrifuge 14, so that it is possible to dispose a plurality of roller pumps in a saved space. Further, according to this configuration, by placing the tubes on the roller pumps and closing the cover body 77, it is possible to easily set the tubes on the roller pumps.

Furthermore, the method for manufacturing the cassette 22 according to the present embodiment includes a molding process of overlaying the first sheet 38 and the second sheet 39 formed by using a soft material which is resistible against the autoclave sterilization, welding the first sheet 38 and the second sheet 39 to form a plurality of flow paths, and molding the cassette 22, and a sterilizing process of performing the autoclave sterilization on the cassette 22 obtained by the molding process. It is possible to manufacture the cassette 22 at low cost compared to the conventional cassette made of the hard resin manufactured by injection molding.

In case of the present embodiment, in the sterilizing process, the bags (the ACD solution bag 24) which contain a liquid is also subjected to the autoclave sterilization together with the cassette 22, so that it is possible to efficiently sterilize the blood sampling circuit set 12 including the cassette 22 and the bags. The conventional cassette is formed by using a material to which autoclave sterilization is not applicable and therefore is sterilized by EOG sterilization, an ACD solution bag to which the EOG sterilization is not applicable is subjected to the autoclave sterilization, and therefore efficiency is poor. Hence, the cassette and the ACD solution bag are separately sterilized and connected or are connected in case of field use. By contrast with this, in the present embodiment, the ACD solution bag 24 is connected to the cassette 22 during the manufacturing process and is subjected to the autoclave sterilization together with the cassette 22, so that it is possible to efficiently manufacture the blood sampling circuit set 12.

Second Embodiment

Figure 8:
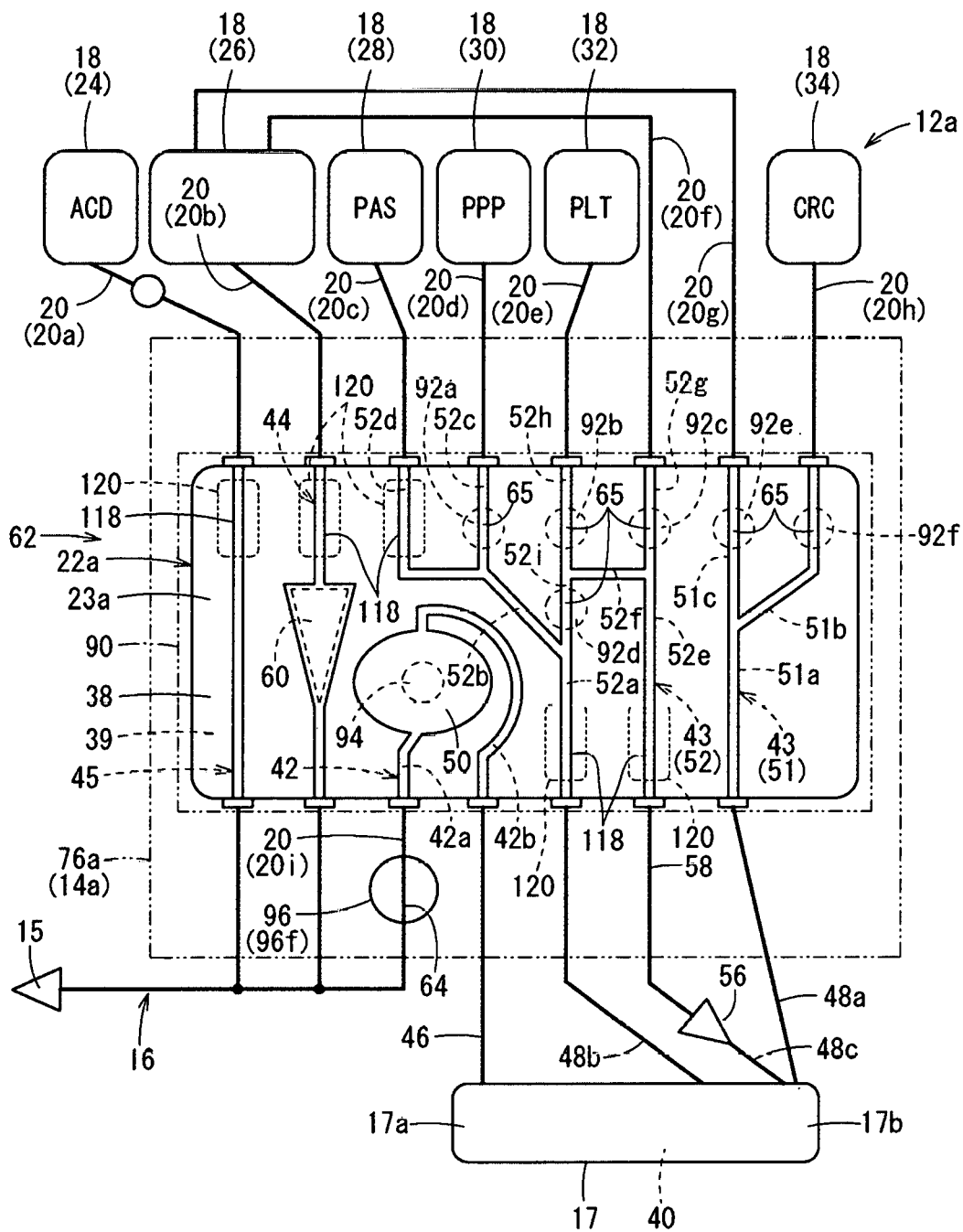
FIG. 8 illustrates a circuit configuration diagram of a blood component sampling system according to a second embodiment of the present disclosure.

Next, differences of a blood component sampling system 10B according to the second embodiment of the present disclosure illustrated in FIG. 8 from a blood component sampling system 10A according to the first embodiment will be mainly described. This blood component sampling system 10B includes a blood sampling circuit set 12a including a blood component sampling cassette 22a (referred to as a "cassette 22a" below), and a centrifuge 14a (see FIG. 9) to which the blood sampling circuit set 12a is attached.

The blood sampling circuit set 12a includes a cassette main body 23a having a plurality of flow paths, and the cassette main body 23a is bonded to overlay a first sheet 38 and a second sheet 39 in a thickness direction and form a plurality of flow paths. Similar to a plurality of flow paths of a cassette main body 23 according to the first embodiment, a plurality of flow paths of the cassette main body 23a includes an introduction line 42, a blood component transfer line 43, a retransfusion line 44, and an ACD solution line 45.

Pump function portions 118 on which pumps 120 of the centrifuge 14a work are provided in an area which is an inflow side of a plurality of flow paths in the cassette main body 23a. In the present embodiment, the pump function portions 118 are provided in an upstream side area of the ACD solution line 45, an upstream side area of the retransfusion line 44 and an upstream side area of a second line 52 (upstream areas of flow path elements 52a, 52d and 52e).

At least a pump function portion 64 among flow path formation portions in the cassette main body 23a bulges in a protrusion shape in the thickness direction of the cassette main body 23a in a normal state where a positive pressure is not applied. In this regard, a portion closer to a downstream side of the flow path formation portions in the cassette main body 23a than the pump function portion 64 is nearly flat in the normal state where the positive pressure is not applied, yet may be formed to bulge in the protrusion shape when the positive pressure is applied.

Figure 9:
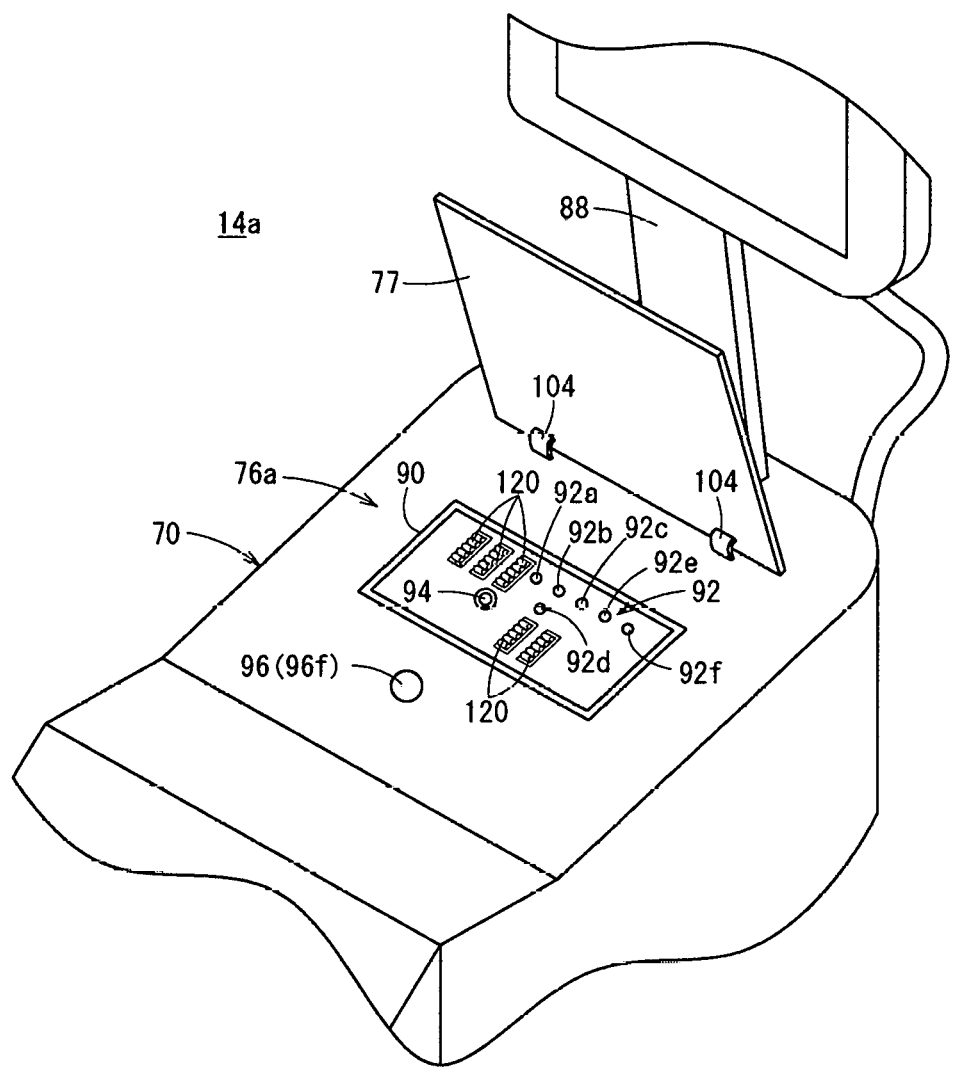
FIG. 9 illustrates a perspective view that illustrates a configuration of an attachment portion of a centrifuge in the blood component sampling system illustrated in FIG. 8.

As illustrated in FIGS. 8 and 9, an attachment portion 76a of the centrifuge 14a includes the pumps 120 disposed in a cassette holding portion 90 instead of pumps 96 in a centrifuge 14 according to the first embodiment. Each pump 120 is configured to cause a liquid (blood components and the like) in the cassette 22a to flow by pressing the pump function portions 118 of the cassette 22a in a state where the pumps 120 are held in the cassette holding portion 90.

Figure 10:
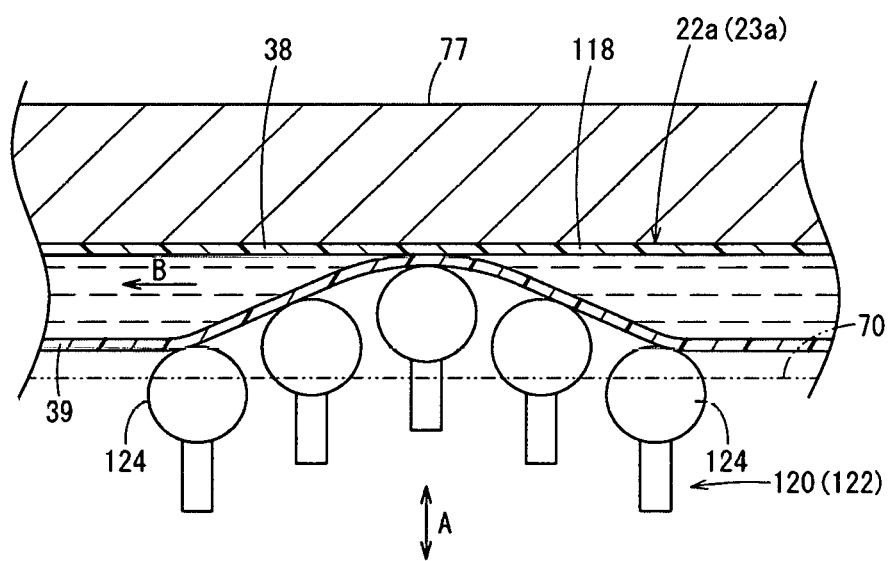
FIG. 10 is a view for explaining a finger pump function provided to the centrifuge.

In the present embodiment, as illustrated in FIG. 10, the pumps 120 adopt a mode of finger pumps 122 including a plurality of finger portions 124 (movable pressing bodies). A plurality of finger portions 124 is configured to move back and forth in the thickness direction (arrow A direction) of the cassette 22a attached to the attachment portion 76a. The finger pumps 122 can cause the fluid to flow in an arrow B direction by sequentially shifting positions of the pump function portions 118 to be crushed by using a plurality of finger portions 124, from a right to a left in FIG. 10. By operating the pump 120, a positive pressure is applied to the side closer to the downstream than the pump 120 in each flow path (ACD solution line 45, the retransfusion line 44 and the second line 52) formed in the cassette main body 23a is.

According to the cassette 22a employing the above configuration, too, similar to a cassette 22 according to the first embodiment, the cassette 22a can be efficiently manufactured at low cost, and the flow paths formed in the cassette main body 23a are not closed during pump operation and do not cause a trouble for fluid transfer of bloods and the like. Further, the pump function portions 118 are automatically set to the pumps 120 when the cassette 22a is attached to the centrifuge 14a, so that it is possible to more efficiently attach the cassette 22a according to the present embodiment to the centrifuge 14a.

In this regard, portions in the second embodiment common to those in the first embodiment provide the same or similar function and effect as those of the first embodiment.

The present disclosure is not limited to the above embodiments, and can be variously modified without departing from the spirit of the present disclosure.

REFERENCE SIGNS LIST

10A, 10B BLOOD COMPONENT SAMPLING SYSTEM
12, 12a BLOOD SAMPLING CIRCUIT SET
14, 14a CENTRIFUGE
22, 22a CASSETTE
23, 23a CASSETTE MAIN BODY
38 FIRST SHEET
39 SECOND SHEET
42 INTRODUCTION LINE
43 BLOOD COMPONENT TRANSFER LINE
44 RETRANSFUSION LINE
64, 118 PUMP FUNCTION PORTION
96, 120 PUMP

The invention claimed is:

1. A blood component sampling cassette comprising:
   a cassette main body having a plurality of flow paths, the cassette main body comprising:
      a first sheet comprising a first portion of the plurality of flow paths formed therein, the first portion of the plurality of flow paths extending from a planar surface of the first sheet; and
      a second sheet comprising a second portion of the plurality of flow paths formed therein, the second portion of the plurality of flow paths extending from a planar surface of the second sheet, wherein the first sheet is overlaid with and bonded to the second sheet along the planar surface of the first sheet and the planar surface of the second sheet, and wherein the first portion of the plurality of flow paths align with the second portion of the plurality of flow paths forming the plurality of flow paths,
   wherein the plurality of flow paths comprises:
      an introduction line configured to introduce a blood of a blood donor;
      a blood component transfer line configured to transfer to a sampling container a blood component obtained by separating the blood;

a retransfusion line configured to transfer to the blood donor at least part of the blood component obtained by the separation; and at least one port member disposed in each of the introduction line, the blood component transfer line, and the retransfusion line, wherein the at least one port member is disposed between the first sheet and the second sheet, and wherein the first sheet and the second sheet are bonded to the at least one port member, wherein the first sheet and the second sheet are each formed of a flexible material that is compatible with autoclave sterilization, and wherein the cassette main body is configured to connect to a plurality of tubes in communication with the plurality of flow paths, respectively, via the at least one port member, wherein the introduction line includes:
  a balloon region; and
  a single flow path of the plurality of flow paths, the single flow path including:
    a first flow path element disposed between a first port member of the introduction line and the balloon region; and
    a second flow path element disposed between a second port member of the introduction line and the balloon region, wherein the balloon region comprises a volume disposed between the first sheet and the second sheet, wherein the balloon region is moveable between an expanded and a contracted state, and wherein the first port member of the introduction line and the second port member of the introduction line are disposed along a first edge of the cassette main body.

2. The blood component sampling cassette according to claim 1, further comprising:
  a plurality of pump function portions disposed adjacent the first edge of the cassette main body, wherein a positive pressure is applied downstream from the plurality of pump function portions by driving pumps in contact with the plurality of pump function portions.

3. The blood component sampling cassette according to claim 2, wherein at least one of the plurality of pump function portions bulges in a normal state.

4. A blood sampling circuit set comprising:
  a blood component sampling cassette configured to detachably attach to a blood component separating device;
  a separating processing unit connected to the blood component sampling cassette by a tube, the separating processing unit including a processing chamber configured to separate blood into a plurality of blood components by operating the blood component separating device; and
  a bag connected to the blood component sampling cassette by a tube,
  wherein the blood component sampling cassette comprises a cassette main body including a plurality of flow paths, the cassette main body comprising:
    a first sheet comprising a first portion of the plurality of flow paths formed therein, the first portion of the plurality of flow paths extending from a planar surface of the first sheet; and
    a second sheet comprising a second portion of the plurality of flow paths formed therein, the second portion of the plurality of flow paths extending from a planar surface of the second sheet, wherein the first sheet is overlaid with and bonded to the second sheet along the planar surface of the first sheet and the planar surface of the second sheet, and wherein the first portion of the plurality of flow paths align with the second portion of the plurality of flow paths forming the plurality of flow paths,
  wherein the plurality of flow paths comprises:
    an introduction line configured to introduce a blood of a blood donor;
    a blood component transfer line configured to transfer to a sampling container a blood component obtained by separating the blood;
    a retransfusion line configured to transfer to the blood donor at least part of the blood component obtained by the separation; and
    a port member disposed in at least one of the introduction line, the blood component transfer line, and the retransfusion line, wherein the port member is disposed between the first sheet and the second sheet, and wherein first sheet and the second sheet are bonded to the port member,
  wherein the first sheet and the second sheet are each formed of a flexible material that is compatible with autoclave sterilization,
  wherein the introduction line includes:
    a balloon region; and
    a single flow path of the plurality of flow paths, the single flow path including:
      a first flow path element disposed between a first port member of the introduction line and the balloon region; and
      a second flow path element disposed between a second port member of the introduction line and the balloon region, wherein the balloon region comprises a volume disposed between the first sheet and the second sheet, wherein the balloon region is moveable between an expanded and a contracted state, and wherein the first port member of the introduction line and the second port member of the introduction line are disposed along a first edge of the cassette main body.

5. A blood component sampling system comprising:
  a blood component separating device; and
  a blood component sampling cassette configured to detachably attach to the blood component separating device,
  wherein the blood component sampling cassette comprises a cassette main body having a plurality of flow paths, the cassette main body configured to detachably attach to the blood component separating device, the cassette main body comprising:
    a first sheet comprising a first portion of the plurality of flow paths formed therein, the first portion of the plurality of flow paths extending from a planar surface of the first sheet; and
    a second sheet comprising a second portion of the plurality of flow paths formed therein, the second portion of the plurality of flow paths extending from a planar surface of the second sheet, wherein the first sheet is overlaid with and bonded to the second sheet along the planar surface of the first sheet and the planar surface of the second sheet, and wherein the first portion of the plurality of flow paths align with the second portion of the plurality of flow paths forming the plurality of flow paths,
  wherein the plurality of flow paths comprises:

an introduction line configured to introduce a blood of a blood donor;

a blood component transfer line configured to transfer to a sampling container a blood component obtained by separating the blood;

a retransfusion line configured to transfer to the blood donor at least part of the blood component obtained by the separation; and a plurality of port members disposed in at least one of the introduction line, the blood component transfer line, and the retransfusion line, wherein the plurality of port members is disposed between the first sheet and the second sheet, and wherein the first sheet and the second sheet are bonded to the plurality of port members, wherein the first sheet and the second sheet are each formed of a flexible material that is compatible with autoclave sterilization, wherein the cassette main body is connected to a plurality of tubes in communication with the plurality of flow paths, respectively, via the plurality of port members, wherein the introduction line includes:
a balloon region; and
a single flow path of the plurality of flow paths, the single flow path including:
a first flow path element disposed between a first port member of the introduction line and the balloon region; and
a second flow path element disposed between a second port member of the introduction line and the balloon region, wherein the balloon region comprises a volume disposed between the first sheet and the second sheet, wherein the balloon region is moveable between an expanded and a contracted state, and wherein the first port member of the introduction line and the second port member of the introduction line are disposed along a first edge of the cassette main body.

6. The blood component sampling system according to claim 5, further comprising:
a plurality of pump function portions disposed adjacent the first edge of the cassette main body, wherein positive pressure is applied downstream from the plurality of pump function portions as pumps press the plurality of pump function portions.

7. The blood component sampling system according to claim 6, wherein the pumps are configured and disposed to press an area of the plurality of flow paths of the cassette main body, and
wherein a portion of the cassette main body pressed by the pumps bulges in a normal state.

8. A method for manufacturing a blood component sampling cassette, the method comprising:
providing a first sheet comprising a first portion of a plurality of flow paths formed therein, the first portion of the plurality of flow paths extending from a planar surface of the first sheet;
providing a second sheet comprising a second portion of the plurality of flow paths formed therein, the second portion of the plurality of flow paths extending from a planar surface of the second sheet;
overlaying the first sheet and the second sheet such that the planar surface of the first sheet contacts the planar surface of the second sheet and the first portion of the plurality of flow paths aligns with the second portion of the plurality of flow paths, wherein the first sheet and the second sheet are each formed of a flexible material compatible with autoclave sterilization;

disposing at least one port member between the first sheet and the second sheet at least partially within the first portion of the plurality of flow paths and the second portion of the plurality of flow paths;

welding the first sheet and the second sheet along the planar surface of the first sheet and the planar surface of the second sheet to form a cassette main body with the plurality of flow paths comprising the at least one port member bonded thereto; and performing autoclave sterilization on the blood component sampling cassette, wherein the plurality of flow paths comprises:
an introduction line configured to introduce a blood of a blood donor;
a blood component transfer line configured to transfer to a sampling container a blood component obtained by separating the blood; and
a retransfusion line configured to transfer to the blood donor at least part of the blood component obtained by the separation, wherein the introduction line includes:
a balloon region; and
a single flow path of the plurality of flow paths, the single flow path including:
a first flow path element disposed between a first port member of the introduction line and the balloon region; and
a second flow path element disposed between a second port member of the introduction line and the balloon region, wherein the balloon region comprises a volume disposed between the first sheet and the second sheet, wherein the balloon region is moveable between an expanded and a contracted state, and wherein the first port member of the introduction line and the second port member of the introduction line are disposed along a first edge of the cassette main body.

9. The method according to claim 8, wherein the performing of autoclave sterilization further comprises subjecting a bag connected to the blood component sampling cassette by a tube and containing a liquid, to the autoclave sterilization together with the blood component sampling cassette during the sterilization.

10. The method according to claim 8, wherein the welding of the first sheet and the second sheet includes a welding process selected from among high frequency welding, ultrasonic welding and thermal welding.

11. The method according to claim 8, wherein the flexible material comprises at least one of polyvinyl chloride and polyolefin.

12. The blood component sampling cassette according to claim 1, wherein the at least one port member extends from an area inside a periphery of the cassette main body to an area outside of the periphery of the cassette main body.

13. The blood component sampling cassette according to claim 12, wherein the retransfusion line further comprises:
a filter disposed between a first port of the retransfusion line and a second port of the retransfusion line, wherein the filter is disposed between the first sheet and the second sheet within the periphery of the cassette main body, and wherein the first sheet and the second sheet are bonded to the filter.

14. The blood component sampling cassette according to claim 13, wherein the introduction line, the blood component transfer line, and the retransfusion line are separate lines.

15. The blood component sampling cassette according to claim 14, wherein, in a plan view, the balloon region is between the filter and the blood component transfer line.

16. The blood component sampling cassette according to claim 15, wherein the first port member of the introduction line and the second port member of the introduction line are immediately adjacent to one another along the first edge of the cassette main body.

17. The blood component sampling cassette according to claim 16, wherein the first port of the retransfusion line is disposed on the first edge of the cassette main body, wherein the second port of the retransfusion line is disposed on a second edge of the cassette main body, wherein the second edge is disposed opposite the first edge, and wherein the retransfusion line extends from the first port to the second port.

18. The blood component sampling cassette according to claim 17, wherein the blood component transfer line extends from the first edge of the cassette main body to the second edge of the cassette main body.

19. The blood component sampling cassette according to claim 1, wherein pump function portions configured to cooperate with pumps of an apheresis machine are positioned at an inflow side of the plurality of flow paths of the cassette main body.

20. The blood component sampling system according to claim 5, wherein pump function portions configured to cooperate with pumps of the blood component separating device are positioned at an inflow side of the plurality of flow paths of the cassette main body.

* * * * *